United States Patent [19]

McAllister

[11] Patent Number: 5,007,730
[45] Date of Patent: Apr. 16, 1991

[54] METHOD AND APPARATUS FOR MEASURING VISION BLOCKAGE RESULTING FROM GLARE

[76] Inventors: John A. McAllister, 7810 Overbrook, Houston, Tex. 77063; Tim C. Taylor, 4140 Southwest Freeway, No. 208, Houston, Tex. 77027

[21] Appl. No.: 220,892

[22] Filed: Jun. 16, 1988

Related U.S. Application Data

[63] Continuation of Ser. No. 835,796, Mar. 3, 1986, abandoned.

[51] Int. Cl.$^5$ ............................ A61B 3/02; A61B 3/10
[52] U.S. Cl. ...................................... 351/243; 351/221
[58] Field of Search ................ 351/221, 222, 237, 243

[56] References Cited

U.S. PATENT DOCUMENTS

3,684,355  8/1972  Molner ............................ 351/22 X
4,155,632  5/1979  Wolbarsht ........................... 351/243

OTHER PUBLICATIONS

E. Wolf, "Glare and Age," Archives of Opthamology, Oct., 1968, vol. 64, pp.502–514.
D. Miller et al, "Glare Sensitivity Related to Use of Contact Lense," Archives of Opthamology, Oct., 1967, vol. 78, pp. 448–450.
D. Miller et al., "Laboratory Evaluation of a Clinical Glass Tester," Archives of Opthamology, Mar., 1972, vol. 87, pp. 324–332.
The Old Eye Chart May Soon Do a Slow Fade, p. 65, July 15, 1985, Business Week.
Brochure, TVA Revolutionizes Refracting, 1985.
Brochure, Glare Testing/ What's the Difference.
Brochure, Aeronautical Model/The Titmus Vision Tester.

*Primary Examiner*—Rodney B. Bovernick

[57] ABSTRACT

A method is disclosed for measuring glare-induced vision blockage in a subject, as are apparatus for performing the method. According to the method, a glare-inducing light is shined in the subject's eyes. A series of visually-perceivable patterns of varying apparent sizes, each pattern arranged around the light, is presented to the subject. Each pattern comprises a sequence of alternating light and dark segments. The pattern is preferably in the form of a broken outline of a circle centered on a window through which the glare-inducing light passes. For each pattern presented, the subject is asked to indicate which if any dark segments he perceives. The subject may also be asked how many dark segments he sees and in what locations. The smallest pattern whose dark segments can be perceived by the subject indicates the size of the subject's glare-induced vision blockage.

2 Claims, 1 Drawing Sheet

METHOD AND APPARATUS FOR MEASURING VISION BLOCKAGE RESULTING FROM GLARE

This application is a continuation of application Ser. No. 835,796, filed Mar. 3, 1986 now abandoned.

BACKGROUND OF THE INVENTION

This invention relates to a method and apparatus for measuring the amount by which glare blocks a person's vision as a result of disperson of light as perceived in the subject's eye.

When a person looks at a light source, e.g., an oncoming automobile headlight, the incoming light rays can be dispersed through the eye due to various eye conditions such as cataracts, intraocular lens implants, the presence of a contact lens or spectacle lenses, and anatomic changes of the corneal surface. In dark surroundings this dispersion can substantially interfere with the eye's ability to detect and resolve other objects, e.g., road boundaries or street signs. A point source of light at a distance may cause what may be referred to as "blocking glare."

The problem of blocking glare may be especially severe in subjects having cataracts. An abnormally high degree of vision impairment arising from blocking glare can indicate the onset of cataract formation.

The blocking effect of glare has been detected by measuring the resulting reduction in visual acuity. Variations on the so-called Snellen method, for example, entail asking the subject to read lines on a conventional eye chart while a light source is directed into his eyes. Similarly, the Miller-Nadler method calls for the subject to identify the orientation of an object (e.g., the letter "C") while a peripheral light source simulates daytime glare. The Terry method calls for the subject to read an eye chart while subjected to a a glare source. The Ginzburg method generally uses a contrast-sensitivity approach.

The use of diminution of visual acuity as an indicator of the impact of glare, however, is necessarily dependent on the subject's acuity generally, which may vary independently of glare and is concomitantly of less reliabilty than is desirable.

SUMMARY OF THE INVENTION

A method is disclosed for measuring glare-induced vision blockage in a subject, as are apparatus for performing the method.

According to the method, a glare-inducing light is shined in the subject's eyes. A series of visually-perceivable patterns of varying apparent sizes is presented to the subject. Each pattern comprises a sequence of alternating light and dark segments. The pattern is preferably in the form of a broken outline of a circle centered on a window through which the glare-inducing light passes.

For each pattern presented, the subject is asked to indicate which if any dark segments he perceives. The subject may also be asked how many dark segments he sees and in what locations.

The smallest pattern whose dark segments can be perceived by the subject indicates the size of the subject's glare-induced vision blockage.

BRIEF DESCRIPTION OF THE DRAWINGS

Throughout the following detailed description, similar reference numerals refer to similar elements in all Figures of the drawings.

DETAILED DESCRIPTION OF SPECIFIC EMBODIMENTS

Figure 1:
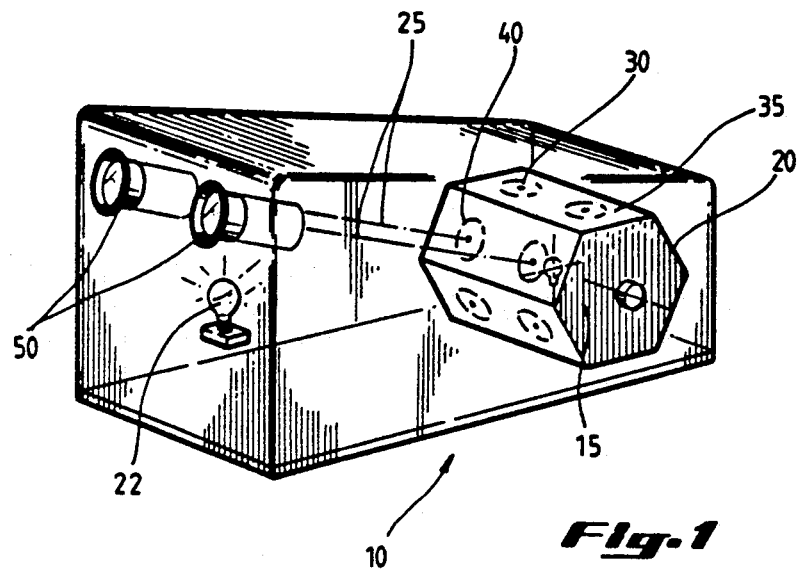
FIG. 1 is a side cutaway view of apparatus in accordance with the invention.

Referring to FIG. 1, a glare measuring apparatus 10 includes a light source 15 mounted within a hollow polygonal cylinder 20 mounted for rotation about an axis oriented normal to a line of vision 25. A non-glare-inducing light source 22, such as a suitably screened, shaded, or frosted bulb, is mounted within the apparatus 10 in front of the cylinder 20 to illuminate the exterior of the cylinder 20. At least one light-passing window 30 is formed in each of several plates 35, each plate 35 forming a face of the cylinder 20.

In the presently preferred embodiment, the light source 15 includes a non-frosted light bulb, oriented so that its filament is visible through the window 30 along the line of vision 25, to simulate glare such as that induced by an oncoming automobile headlight.

Figure 2:
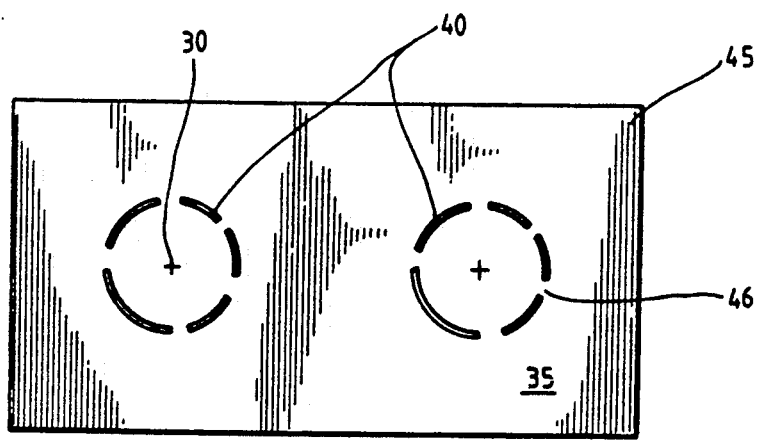
FIG. 2 is a straight-on view of a portion of the apparatus.

A circle 40, centered on the window 30, is displayed on each of at least several of the plates 35. Each of the circles 40 includes a pattern of alternating bright and dark portions. As shown in FIG. 2, the patterns for each circle 40 consist of a circumferential pattern of bright segments 45 painted with white paint (or otherwise drawn or scribed) on the plate 35. Each pair of adjacent bright segments 45 brackets a dark segment or break 46.

In the embodiment shown, each plate 35 includes two identical circles 40, each centered on a window 30. This permits monocular or binocular testing of a subject by blocking off one of two eyepieces 50, as shown in FIG. 1, or neither eyepiece 50, in a manner known to those skilled in the art.

Satisfactory results have been obtained by using a plate 35 approximately 6.5 inches by 2.5 inches by 0.125 inches, painted flat black. On such a plate, the circles 40 have been successfully used by spacing their respective centers approximately 2.625 inches apart, with the associated windows 30 located at said centers, and with a sight-line distance from the inner end of the eyepieces 50 to the circles 40 of approximately 13 inches.

Windows 30 of approximately 2 mm diameter have been found to be satisfactory. Painted white line segments 45 approximately 1 mm wide, circumscribing a circular area approximately 1 cm to 4 cm in diameter with a varying number of breaks 46 each approximately 3 mm long, have also been found to be satisfactory.

The pairs of identical circles 40 on the different plates 35 are preferably varied in the diameters, number of breaks, and orientation of breaks of the circles. Different circles 40 can be presented to the subject by rotating the cylinder 20. Preferably, two pairs of same-diameter circles 40, on two separate plates 35, will be included for each circle diameter; the identical circles 40 on the first such plate 35 will be of the same diameter, but of varying number and/or orientation of breaks, as the identical circles 40 on the second such plate 35.

Operation

The apparatus 10 is operated as follows. The subject's ability to perceive the breaks 46 is first tested under adequate lighting (e.g., from the light source 22), without glare light from the source 15. The subject looks through the eyepieces 50 at the first plate 35 and counts the breaks 46 he sees on the circle 40. The examiner records the subject's response and rotates the cylinder 20 to present a new set of circles 40 for a new subject response. When all circles 40 have been presented, the examiner records the smallest circle 40 whose breaks 46 the subject is able to discern correctly (referred to herein as the minimum circle). This gives an indication whether the subject has sufficient without-glare visual acuity to make with-glare testing meaningful.

The test is then repeated with both light sources 15 and 22 energized. A with-glare minimum circle is determined for these conditions. If a glare problem exists, it is believed that the with-glare minimum circle will be of greater diameter than the minimum circle without glare.

The diameter of the with-glare minimum circle, coupled with the distance between the subject's eyes and the circles 40, gives an indication of the approximate arc within a subject's field of vision of his glare-induced vision blockage. This arc can in turn be used to estimate the size of a subject's "blocking glare blind spot" at various distances, e.g., by linear extrapolation.

For example, a nighttime automobile driver might have a glare-induced blind spot that, at a distance suitable for safe stopping, is too wide for safety. Suppose that a driver, when looking at an oncoming headlight 60 feet away in the opposite lane of a road, has a blind spot that at that distance is ten feet in radius, and that the distance from the headlight to his own lane is only four feet. His glare-induced blind spot thus extends six feet into his own lane. If an object is sitting in his lane within that blind spot, the driver will probably hit it. The apparatus 10 has been used to predict the width of these blind spots. The degree of confidence and specificity of the prediction will of course depend on the resolution capability of the apparatus 10, i.e., the more circles 40 of different sizes can be provided, the more precise will be the prediction.

The apparatus 10 may be provided with two sets of circles 40 on two plates 35 for any given diameter of circle 40, with the circles 40 on any single plate being identical and all four circles 40 being identical except for the number and/or orientation of the breaks 46. Such a provision can help detect spicular glare problems, e.g., spoke-like areas of glare-induced vision impairment radiating approximately from the center of the subject's eye. If a subject can perceive the correct number of breaks 46 on a particular plate 35, but cannot perceive the correct number of breaks 46 on another plate 35 having a circle 40 of the same size but of a different orientation, this indicates the presence of a spicule in the subject's field of vision. If a sufficient number of plates 35 is provided, the apparatus may be used to create a rough map of the spicules.

It will be appreciated by those skilled in the art having the benefit of this disclosure that this invention is believed to be capable of application in other situations. Accordingly, this description is to be construed as illustrative only and as for the purpose of teaching those skilled in the art the manner of carrying out the invention.

It is also to be understood that the form of the invention shown and described is to be taken as the presently preferred embodiment. Various modifications and changes may be made, e.g., in the shape, size, and arrangement of parts, without departing from the spirit and scope of the invention as set forth below in the claims.

For example, in determining the arc of the subject's vision blockage, the distance of the circles 40 from the eyes could be varied while maintaining the circle diameter constant, instead of vice versa as disclosed above. This might permit more precise measurement because of the use of a continuously varying distance instead of a set of discrete diameters as shown above. It is presently believed, however, that the apparatus 10 disclosed herein is easier for an examiner to operate yet still yields satisfactory results for most purposes.

The light sources 15 and 22 may be provided with suitable dimmers and a photometer to enable calibration of the relative intensities of the light sources. This could be useful where bulbs of different intensities are to be used as replacement parts or if a bulb's intensity changes over time.

A computer-controlled graphics screen could be used in place of the plates 35. This would permit the apparatus to display virtually any number of different circle sizes, number of breaks 46, and orientations, permitting greater and greater precision in measuring or mapping any areas of glare-induced vision impairment.

The subject may be asked to indicate the number of breaks 46 he sees on a given circle 40, or additionally to describe their locations. This can give further data for use in mapping the subject's glare problems.

It is intended that the following claims be interpreted to embrace all such modifications and changes.

What is claimed is:

1. Apparatus for measuring glare-induced vision blockage in a subject, said apparatus comprising:
   a hollow polygonal cylinder mounted for rotation about a longitudinal axis;
   each face of said cylinder comprising a plate;
   each said plate having a light-passing window formed therein;
   a viewer arranged to permit said subject to perceive at least one said plate;
   a light source interior to said cylinder;
   a pattern of alternating light and dark segments arranged about each said window;
   said patterns being of varying actual sizes; and
   an arm adapted to selectively rotate said cylinder.

2. The apparatus of claim 1, wherein said pattern comprises the outline of a circle.

* * * * *